United States Patent [19]

Shoher et al.

[11] 4,318,697

[45] Mar. 9, 1982

[54] DENTAL RESTORATIVE ANTERIOR STRUCTURE

[76] Inventors: Itzhak Shoher, 50 Shlomo Hamelech St., Tel Aviv; Aharon E. Whiteman, 13 J1 Perez St., Petach Tikvah, both of Israel

[21] Appl. No.: 167,712

[22] Filed: Jul. 11, 1980

Related U.S. Application Data

[63] Continuation-in-part of Ser. No. 8,944, Feb. 2, 1979.

[51] Int. Cl.³ .............................................. A61C 13/08
[52] U.S. Cl. ..................................... 433/208; 433/167
[58] Field of Search ................................ 433/206, 208

[56] References Cited

FOREIGN PATENT DOCUMENTS 273248  1/1951  Switzerland ..................... 433/208

*Primary Examiner*—Robert Peshock

[57] ABSTRACT

The dental restorative structure of the present invention comprises a porcelain superstructure surrounding a metal substructure composed of a framework of relatively thin metal rod-like members. The rod-like members extend gingivally from a relatively crescent shaped member. An additional upright brace extends toward the incisal edge of the restoration and includes an opening for forming a porcelain pocket between the brace and the crescent shaped member.

7 Claims, 4 Drawing Figures

FIG. 1
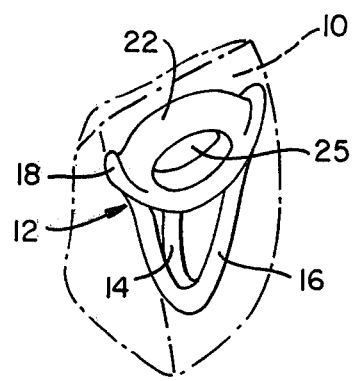
FIG. 2
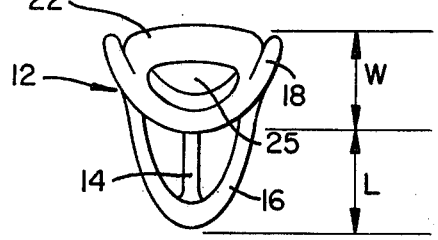
FIG. 4
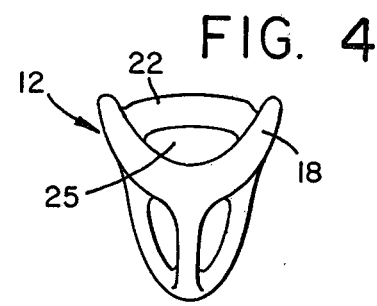
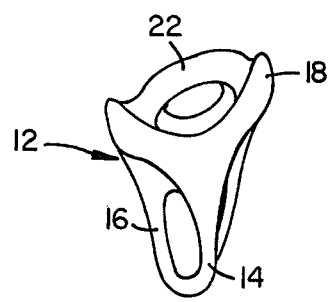
FIG. 3

DENTAL RESTORATIVE ANTERIOR STRUCTURE

This is a continuation-in-part application of U.S. application Ser. No. 8,944, filed Feb. 2, 1979 entitled Dental Restorative Structures.

This invention relates to a porcelain fused to metal structure having a ceramic porcelain superstructure and a metal substructure and to a preformed coping design for an anterior dental restoration.

The porcelain to metal dental restoration has become a widely used restoration in fixed prosthodontics. Dental porcelain has excellent optical properties closely simulating the enamel of natural teeth and is readily shaped and arranged to obtain an esthetic quality conforming the restoration to the original tooth. However, porcelain to metal restorations are presently known to experience fracture despite the attention given to their construction. The failure of the porcelain to metal restoration through fracture cannot be explained away by simply attributing it to excessive masticating forces or to unwarranted esthetic concessions during construction.

The construction of a restoration is based upon principles and techniques developed over a great many years. Extensive investigation of construction variables have, in general, been limited to the selection of materials, material composition and characteristics, preparation of the metal surface to assure a satisfactory bond between the metal and porcelain interface and the design and construction of the metal substructure. The metal substructure, which is alternatively referred to in the dental arts as the metal framework or base support, must be sufficiently rigid so as not to deform under the application of force and must be fabricated following proper procedures in order to provide an effective seal between the metal substructure and the prepared tooth form. To satisfy the latter requirement meticulous atrention is given to the preparation of the impression, fabrication of the die, formation of the wax pattern, investing procedure and casting method.

Little attention has heretofore been given to the exterior geometry of the metal substructure, i.e., the substructure surface geometry which interfaces with the fused porcelain superstructure. In accordance with current practice the wax or plastic pattern, commonly referred to as the coping, is formed with an exterior "thimble" or "cupsed thimble" shaped geometry. A "thimble shape" coping can be visualized as a quadrilaterial pyramid with a frustoconical cross-section whereas the "cupsed thimble shape" coping is similar to the thimble shape with raised regions corresponding to the cusps in the crown.

The principal determination in the selection of the coping for a crown or pontic is currently based upon providing as much metal bulk as possible particularly for the pontic. Present practice also dictates forming rounded convex edges whenever possible. The use of a reinforcing collar about the gingival margin is further recommended for added strength.

Applicants corresponding application Ser. No. 8,944 entitled "Dental Restorative Structures" filed on Feb. 2, 1979, the disclosure of which is herein incorporated by reference, is directed to various designs for the restorative crown, pontic and bridgework both for anterior and posterior teeth. Applicants present invention is specifically directed to an improved design for an anterior pontic and bridgework and more specifically to the pontic or bridgework structure. The present invention is also applicable to the design of the coping for use in constructing the substructure for a porcelain fused to metal restoration as well as a denture or partial denture.

In a conventional pontic design the substructure is a solid mass of metal. In accordance with the design principals of the present invention, which is in conformity with the teachings of Applicants corresponding application referred to above, very little metal is needed to fabricate the pontic. The pontic of the present invention has a substructure comprising an assembly of integrally connected metal rod like members to improve the fracture resistance to impact and pressure forces. The rods extend gingivally from a relatively crescent shaped metal member disposed in the restoration to provide a large incisal concavity. An additional metal brace extends from the relatively crescent shaped member in a substantially upright direction toward the incisal edge of the restoration. The metal brace has a relatively large opening for providing a porcelain pocket between the brace and the relatively crescent shaped member. The porcelain superstructure surrounds the substructure and fills the spaces separating the metal rods from one another and the opening between the metal brace and the relatively crescent shaped metal member. The porcelain restoration thus formed has superior strength relative to the conventional porcelain fused to metal pontic and possesses substantially greater resistance to fracture from impact or pressure.

Other advantages of the present invention will become apparent from the following detailed description of the invention when read in conjunction with the accompanying drawings of which:

FIG. 1 is a perspective view of the anterior pontic dental restoration in accordance with the present invention viewed from the buccal side with the procelain superstructure shown in a transparent silhouette;

FIG. 2 is a plan view of FIG. 1 viewed from the buccal side;

FIG. 3 is another perspective view of the pontic restoration of the present invention viewed from the lingual side; and FIG. 4 is a plan view of the pontic of FIG. 3 viewed from the lingual side.

The pontic dental restoration as shown in FIGS. 1–4 includes a porcelain superstructure 10 and a metal substructure 12. The porcelain used in forming the superstructure may be composed from any conventional dental porcelain composition containing a mixture of feldspar, kaolin and quartz. The porcelain is fired over the metal substructure 12 in successive layers and cured in a heated furnace following any conventional procedure well known in the art. The porcelain superstructure 10 completely surrounds the substructure 12 and occupies the spaces between and around the open framework of members forming the metal substructure 12.

Although any metal composition may be used in forming the substructure 12 the preferred metal composition should possess desirable physical characteristics which will resist deformation under normal force conditions experienced in the mouth and interfere as little as possible with the esthetics of the restoration. The selected composition may be any known conventional precious or semi-precious metal alloy or any one of the conventional non-precious metal alloys suitable for use in a dental restoration.

The members 14, 16, 18 and 22 forming the substructure 12 are integrally connected to form a structural framework for the porcelain superstructure. The members 14 and 16 are preferably thin rod shaped members. The rod 16 is looped in the shape of a "U" on the buccal side of the restoration and depends gingivally from a relatively crescent shaped member 18 which lies in a mesial distal plane within the restoration. The rod 14 joins the rod 16 to the crescent shaped member 18 occluso-cervically. The rod 14 is preferably arched with a slightly concave shape and forms in conjunction with the rod 16 a concave base in the configuration of an inverted tripod. The crescent shaped member 18 also has a concave curvature which forms a basin to provide a relatively large occlusal concavity in the porcelain superstructure 10. An additional thin metal brace 22 extends upright from the crescent shaped member 18 toward the incisal edge of the restoration. The metal brace 22 has a relatively large opening 25 for forming a porcelain pocket between the metal brace 22 and the relatively crescent shaped member 18. The porcelain superstructure fills the voids provided around and between the rods 14 and 16 and the area within the opening 25. The porcelain occupying the opening 25 is placed in compression which acts to prevent the brace 22 from receding and separating from the porcelain during the curing state. The brace 22 provides resistance to impact and pressure forces which are directed at the incisal edge in either the buccal or lingual directions.

The rods 14 and 16 extend a distance "L" measured gingivally from the symmetrical center of the crescent shaped member 18, which will vary relative to the distance "W" of the metal brace 22, measured incisally from the same relative central point on member 18, depending upon the size of the anterior tooth to be restored. Moreover, the extent of the curvature in the relatively crescent shaped member 18 is also dependent on the tooth size and is not critical to the present invention. Of primary importance to the present invention is placing the porcelain in a state of compression within the dental restoration. It is this state of compression that is primarily responsible for the substantial increase in the resistance to porcelain fracture independent of the porcelain composition. A compressive state is developed even when using only the framework of rods because of the differences in thermal contraction rates between the metal rods snd the surrounding porcelain. The surrounding porcelain prevents the metal rods from shrinking which results in compression of the porcelain at the interface. The concave geometries prevent the metal from pulling away at the metal porcelain interface and acts to place the entire porcelain body under compression. With the entire porcelain body under compression there is no area vulnerable to fracture. Moreover, in accordance with the construction of the present invention the upright brace protects against forces directed buccally or lingually.

The metal substructure 12 of the present invention is constructed in a conventional manner starting from a wax or plastic coping having a duplicate exterior configuration. The wax or plastic coping for the substructure may be prefabricated in a conventional fashion into the configuration of the present invention for immediate use by a dental laboratory. In forming the metal substructure from a preformed wax or plastic coping, the coping is invested following a conventional procedure such as the "lost-wax" technique to form a duplicate metal substructure. Any conventional wax or plastic composition may be used for making a preformed wax or plastic coping.

What is claimed is:

1. A dental restoration comprising an anterior pontic having a porcelain superstructure surrounding a metal framework composed of an integral assembly of metal rod-like members extending gingivally from a relatively curved metal member extending mesial-distally within the restoration and further including an upright member extending rearward the incisal edge of said restoration with an opening for providing a pocket of porcelain between the upright member and the relatively curved metal member.

2. A dental restoration as defined in claim 1 wherein said relatively curved metal member has a generally crescent shape extending toward the mesial and distal edges of the restoration.

3. A dental restoration as defined in claim 2 wherein said upright metal member is a thin plate-like member having an opening.

4. A dental restoration as defined in claim 3 wherein said upright metal member is curved.

5. A dental restoration as defined in claim 3 wherein said metal rod-like members comprise a first member looped in the shape of a "U" on the buccal side of the restoration and a second member joining the first member to the curved member occluso-cervically.

6. A dental coping for forming the metal framework of a pontic in a dental restoration comprising an integral assembly of rod-like members interconnected in an open structural arrangement and depending from a relatively crescent shaped member, with a first one of said rod-like members being looped in a shape of a "U" and with a second rod-like members being joining said first member to said relatively crescent shaped member occluso-cervically with each of said members being composed of a material selected from the class consisting of wax or plastic.

7. A dental coping as defined in claim 6 further comprising a third member extending relatively upright from said relatively crescent shaped member and having an open area therebetween.

* * * * *